US007199129B2

(12) United States Patent
Jackson et al.

(10) Patent No.: US 7,199,129 B2
(45) Date of Patent: Apr. 3, 2007

(54) DERIVATIVES OF MORPHINE-LIKE OPIOID COMPOUNDS

(75) Inventors: William Roy Jackson, Camberwell (AU); Kamani Rupika Subasinghe, Glen Waverley (AU)

(73) Assignees: Monash University, Clayton (AU); Neuro Therapeutics Limited, Toorak (AU)

( * ) Notice: Subject to any disclaimer, the term of this patent is extended or adjusted under 35 U.S.C. 154(b) by 148 days.

(21) Appl. No.: 10/486,536

(22) PCT Filed: Aug. 9, 2002

(86) PCT No.: PCT/AU02/01088

§ 371 (c)(1),
(2), (4) Date: Jun. 21, 2004

(87) PCT Pub. No.: WO03/014122

PCT Pub. Date: Feb. 20, 2003

(65) Prior Publication Data

US 2004/0242616 A1 Dec. 2, 2004

(30) Foreign Application Priority Data

Aug. 10, 2001 (AU) .................................... PR 6938
Dec. 19, 2001 (AU) .................................... PR 9640

(51) Int. Cl.
*A61K 31/485* (2006.01)
*C07D 489/02* (2006.01)

(52) U.S. Cl. .......................... 514/282; 546/44; 546/45; 546/46; 546/39; 546/74; 514/279; 514/289

(58) Field of Classification Search ................ 514/282, 514/279, 289; 546/44, 45, 46, 39, 61, 74
See application file for complete search history.

(56) References Cited

U.S. PATENT DOCUMENTS 3,341,538 A 9/1967 Block et al.
6,784,186 B1 * 8/2004 Jackson et al. ............. 514/279

FOREIGN PATENT DOCUMENTS

WO WO9938869 8/1999
WO WO 02/18348 A2 3/2002

* cited by examiner

*Primary Examiner*—Charanjit S. Aulakh
(74) *Attorney, Agent, or Firm*—Klarquist Sparkman, LLP

(57) ABSTRACT

The present disclosure concerns compounds of formula (I) and pharmaceutically acceptable salts, hydrates, solvates, pharmaceutically acceptable derivatives, pro-drugs, tautomers and/or isomers thereof. The disclosure also relates to processes for the preparation of compounds according to formula (I), pharmaceutical or veterinary compositions containing such compounds or methods of treatment and/or prophylaxis of a condition or symptom that is inhibited, reduced or alleviated by opioid receptor activation Formula 1

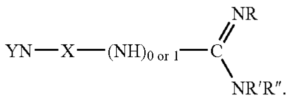

16 Claims, No Drawings

DERIVATIVES OF MORPHINE-LIKE OPIOID COMPOUNDS

CROSS REFERENCE TO RELATED APPLICATIONS

This is the U.S. § 371 National Stage of International Application No. PCT/AU02/01088, filed Aug. 9, 2002, (published in English under PCT Article 21(2)), which in turn claims the benefit of Australian Patent Application No. PR6938, filed Aug. 10, 2001, and Australian Patent Application No. PR9640, filed Dec. 19, 2001.

This invention relates to novel derivatives of compounds with opiate receptor agonist or antagonist activity, such as analgesic or related pharmacological activity. In particular, the invention relates to derivatives of morphine-like opioid compounds in which an amidine or guanidine substituted with at least one aromatic group is linked to the tertiary nitrogen atom of the morphine-like opioid.

BACKGROUND OF THE INVENTION

No admission is made that any reference constitutes prior art. A large range of therapeutic compounds is currently used in the treatment of conditions such as allergies, diarrhoea, migraine and other pain conditions, and in the treatment of congestive heart failure. These compounds include compounds with analgesic or related activities, such as anti-tussives, anti-depressants, local anaesthetics, anti-hypertensives, anti-asthmatics, anti-histamines, and anti-serotonins.

However, many of the therapeutic compounds of the types enumerated above have undesirable side-effects, such as the respiratory depression caused by opiates. In particular, many drugs which are useful for their action on the peripheral nervous system have undesirable effects in the central nervous system.

Thus opiates are the most powerful analgesics known, but their usefulness is greatly limited by their side-effects, including severe respiratory depression, and ability to induce addiction and physical dependence.

Despite intensive efforts to design analogues of morphine and related opioids which retain the analgesic activity, but which do not have a deleterious effect on the central nervous system and the bowel, success has been limited. We have attempted to modify the ability of biologically-active compounds to cross the blood-brain barrier by incorporating a highly polar group into the molecular structure. Thus we have shown that derivatives of the 2N atom of mianserin comprising a guanidino group show $H_1$ and 5-hydroxytryptamine activity, but show no detectable activity in the central nervous system. In contrast, a compound in which the 2N atom of mianserin was substituted with a urea group still showed pronounced central nervous system activity (Jackson et al; Clin. Ex. Pharmacol. Physiol., 1992 19 17–23 and our U.S. Pat. No. 5,049,637).

In our International patent application No. PCT/AU00/00062 (WO99/38869), we showed that compounds obtained by linking a highly charged group to the tertiary nitrogen atom of a morphine-like opioid via a spacer group not only have reduced central side-effects, but retain activity at desired peripheral receptors. We believe that this is a result of the decreased lipophilicity of the compounds, and their resulting decreased ability to penetrate the blood-brain barrier. In particular, those compounds which show activities at opioid receptors retained broad analgesic activity, contrary to the previously accepted state of the art, which teaches that the analgesic effects of morphine-like opioids are mediated from the CNS. The selectivity of these compounds for peripheral opioid receptors not only makes them useful for the treatment of pain without sedative or addictive effects, but also may make them useful for treatment of AIDS and related immune deficiency diseases.

We have now surprisingly found that compounds of this general type in which one or both nitrogen atoms in the amidine or guanidine group are substituted with an aryl group have remarkably high analgesic activity, accompanied by reduced toxicity. These compounds also have the desired decreased ability to penetrate the blood-brain barrier.

SUMMARY OF THE INVENTION

In a first aspect, the invention provides a compound of formula I

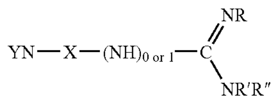

in which

YN is a morphine-like opioid radical;

X is—a direct bond,

- an optionally substituted, branched, straight-chained or cyclic alkylene having from 1 to 6 carbon atoms, optionally containing one or two heteroatoms in the alkyl chain, or
- an optionally substituted, branched or straight-chained alkenylene having from 4 to 10 carbon atoms; and R, R' and R" are independently hydrogen, alkyl, substituted alkyl, alkene, substituted alkene, alkyne, substituted alkyne, aryl, substituted aryl, heterocycle, substituted heterocycle or cyano provided that at least one of R and R' is aryl, substituted aryl, heterocycle or substituted heterocycle;

or a pharmaceutically acceptable salt, hydrate, solvate, pharmaceutically acceptable derivative, pro-drug, tautomer and/or isomer thereof.

Preferably R is H, alkyl, phenyl, substituted phenyl, heterocycle or substituted heterocycle.

Preferably R' is phenyl, substituted phenyl, heterocycle or substituted heterocycle.

Preferably, R" is H, alkyl, phenyl, substituted phenyl, heterocycle or substituted heterocycle.

It is preferred that at least one of R' and R" is not H.

Preferably, at each instance, the heterocycle or substituted heterocycle is heteroaromatic or substituted heteroaromatic, respectively.

Preferably the substituent on the aryl or heteroaryl group is a $C_{1-6}$ alkyl group such as methyl or ethyl, haloalkyl (including di- and tri-haloalkyls, such as trifluromethyl), hydroxy, amino, alkoxy, haloalkoxy, nitro, alkylthio, thiol or halo.

Preferably, the radical YN— is a radical of Formula II or Formula III:

II

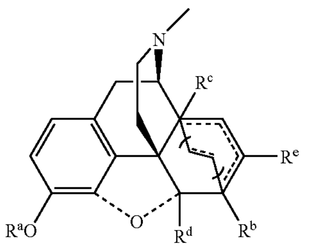

wherein:

$R^a$ is H, $C_{1-4}$ alkyl, $C_{1-4}$ alkanoyl, $C_{1-4}$carboxyalkyl, or an O-protecting group;

$R^b$ is H, OH, protected hydroxy, $C_{1-4}$alkanoyloxy or $C_{1-4}$alkoxy; or, when C6 does not have a double bond to C7, and does not have an endoetheno or endoethano bridge to C14, $R^b$ may be =O or $=CH_2$;

$R^c$ is H, OH or protected hydroxy;

$R^d$ is H or $C_{1-4}$ alkyl;

$R^e$ is H, CN, $C_{1-4}$alkanoyl, $C_{1-4}$alkoxycarbonyl, $C_{2-8}$ alkenyl,

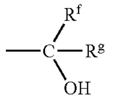

in which $R^f$ is H, alkyl, aryl, or alkaryl, and $R^g$ is $C_{1-8}$ alkyl, $C_{2-6}$alkenyl, $C_{2-6}$alkynyl, each of these three groups being optionally substituted by aryl, or $R^g$ is substituted aryl (the substituent(s) on the aryl group being chosen from halo, alkyl, $C_{1-4}$alkoxy, haloalkyl), tetrahydrofuranyl, $C_{1-4}$ alkoxy;

wherein the oxygen between C4 and C5 may or may not be present, as represented by the broken lines; wherein the brackets around the group between C6 and C14 represents that the group may or may not be present, and when present the group may be an endoetheno or an endoethano bridge, as represented by the broken line; and wherein the dashed line between C6, C7, C8 and C14 represents that there is or are either zero, one or two double bonds, with the one double bond being either between C6 and C7, or C7 and C8, and the two double bonds being between C6 and C7, and C8 and C14;

III

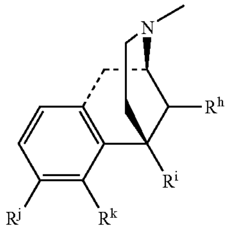

wherein $R^h$ is H or $C_{1-4}$ alkyl;

$R^i$ is H, OH, $C_{1-4}$ alkanoyl or $C_{1-4}$alkyl;

$R^j$ is H, OH, $C_{1-4}$ alkoxy, $C_{1-4}$ alkanoyl, $C_{1-4}$ alkanoyloxy; $C_{1-4}$ carboxyalkyloxy or protected hydroxy; and $R^k$ is H, OH, or protected hydroxy;

and wherein the two dashed lines represent that the two bonds may be both present or both absent.

In one embodiment of the invention, the radical YN— is a radical of formula II.

Preferably, the radical YN— is a radical of a compound selected from the group consisting of morphine, codeine, heroin, ethylmorphine, O-carboxymethylmorphine, O-acetylmorphine, hydrocodone, hydromorphone, oxymorphone, oxycodone, dihydrocodeine, thebaine, metopon, etorphine, acetorphine, ketobemidone, ethoheptazine, diprenorphine (M5050), buprenorphine, phenomorphan, levorphanol, pentazocine, eptazocine, metazocine, dihydroetorphine and dihydroacetorphine.

Preferably the radical YN— is a radical of morphine, codeine, buprenorphine or diprenorphine.

Particularly preferred compounds are as follows:

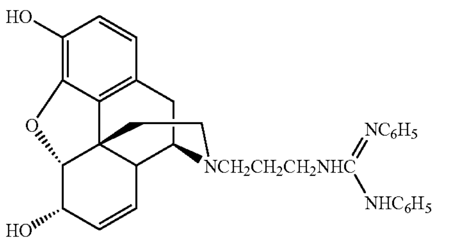

KRS-5-150

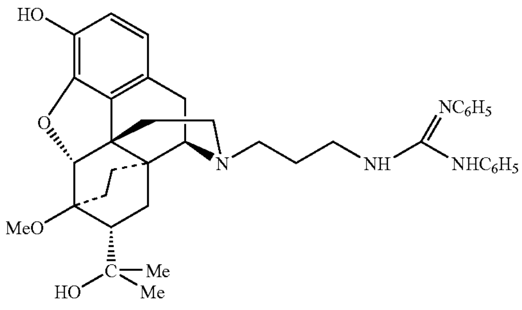

KRS-6-79

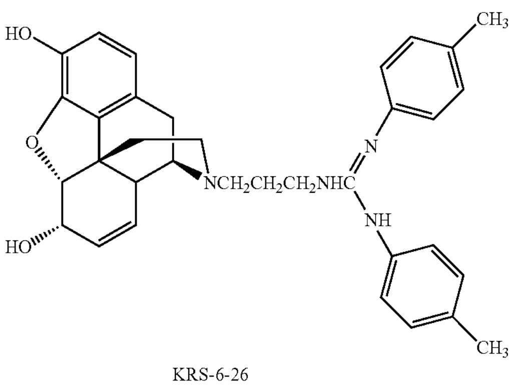

KRS-6-26

-continued

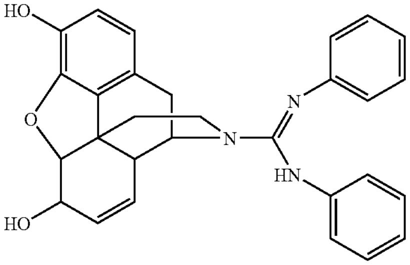

JFY-058

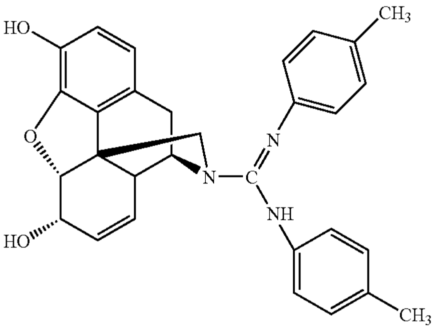

KRS-6-85

In a second aspect, the invention provides a process for the preparation of a compound of formula I defined above which includes the step of:

(a) reacting a precursor for the radical YN—X—(NH)$_{0\ or\ 1}$— with a precursor for the radical

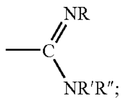

or (b) reacting a precursor for the radical YN— with a precursor for the radical

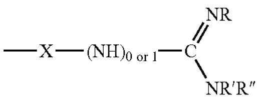

in which YN—, X, R, R' and R" areas defined in formula I.

When the method is conducted via route (a) outlined above, the reaction preferably includes one of the following steps:

(i) reacting YN—H or YN—X—$NH_2$ with a compound of formula

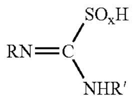

in which x is 2 or 3, to form a compound of Formula I in which R" is H;

(ii) reacting YN—H or YN—X—$NH_2$ with cyanogen bromide to give a cyanamide (YN—CN or YN—X—NH—CN) and then reacting the cyanamide with $R'NH_2Z$ in which Z is an acid addition salt, to form a compound of formula I in which R is H and R" is H;

(iii) reacting YN—H or YN—X—$NH_2$ with RN═C═NR' to form a compound of formula I in which R" is H; or (iv) reacting YN—H or YN—X—$NH_2$ with a compound of formula 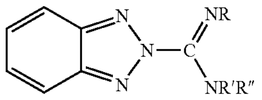 and/or formula 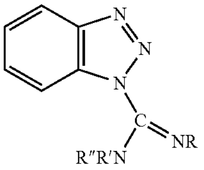

When the method is conducted via route (b) outlined above, the reaction preferably includes the steps of:

(1) reacting the compound [hydroxy protecting group] O—X—$NH_2$ with (i) a compound of formula

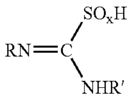

in which x is 2 or 3;

(ii) RN═C═NR'; or (iii) a compound of formula 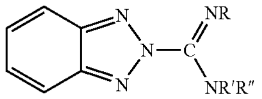 and/or formula 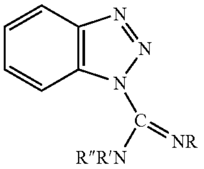

to form a compound of formula IV

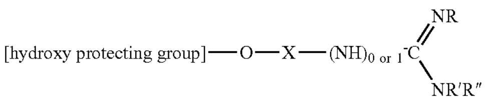

(2) removing the hydroxy-protecting group from the compound of formula IV and brominating the deprotected compound; and (3) reacting the brominated product of the previous step with YN—H to form the compound of formula I.

According to a third aspect, the invention provides a pharmaceutical or veterinary composition comprising a compound according to formula I, together with a pharmaceutically or veterinarily acceptable carrier.

According to a fourth aspect, the invention provides a method of treatment and/or prophylaxis of a condition or symptom that is inhibited, reduced or alleviated by opioid receptor activation, comprising administering a therapeutically effective amount of the compound of formula I to a subject in need thereof. Preferably, the method involves the treatment and/or prophylaxis of pain in the peripheral nervous system with comparably less or no activity on the central nervous system.

According to a fifth aspect, the invention provides a method of inducing analgesia, comprising the step of administering an effective amount of a compound of formula I to a subject in need of such treatment.

According to a sixth aspect, the invention provides the use of a compound of formula I in the manufacture of a medicament for the treatment and/or prophylaxis of a condition or symptom that is inhibited, reduced or alleviated by opioid receptor activiation. Again, the condition or symptom is preferably pain.

The present invention also provides a compound of formula I for use in the treatment and/or prophylaxis of a condition or symptom that is inhibited, reduced or alleviated by opioid receptor activation, such as pain.

The present invention further provides use of a compound for formula I as an analgesic.

The present invention further provides a method of reducing the central nervous system activity of a morphine-like opioid, comprising the step of linking the nitrogen atom of the morphine-like opioid to the radical

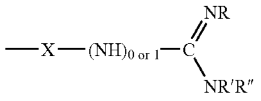

in which X, R, R' and R" are as defined above.

DETAILED DESCRIPTION OF THE INVENTION

We wished to investigate modifications of the preferred compounds described in our earlier application No. PCT/AU00/00062 in order to improve their bioavailability. In these preferred compounds the strongly basic group is guanidine, which is protonated at physiological pH, and is therefore expected to be non-lipophilic and thus unable to penetrate the blood brain barrier. However, the general formula disclosed in PCT/AU00/00062 did not encompass compounds in which the guanidine-moiety was substituted with an aromatic group.

Aryl guanidines were not considered in our earlier study, because the extra carbon atoms in the aromatic rings were expected to make them less lipophilic. Moreover, aromatic ring substitution would lead to lower basicity, and would thus possibly reduce salt formation to such an extent that a significant amount of the free base would be present, so that the compound could penetrate the blood brain barrier. The effect of aromatic ring substitution on the $ID_{50}$ of the most preferred compounds of PCT/AU00/00062, which we refer to as guanidinomorphine compounds, was unknown, but was not expected to be beneficial.

Most unexpectedly we found that when an aromatic ring substituent was added to the guanidine moiety, both the analgesic activity and the $ID_{50}$ increased, without any evidence for the compound entering the central nervous system (CNS). Moreover the aromatic ring substituted compound showed reduced toxicity compared to the earlier compounds.

A number of terms of the art are used in this specification and the claims, and they are described below for complete understanding of the scope of the invention.

The word "comprising" means "including but not limited to", and that the word "comprises" has a corresponding meaning.

The term "aryl" refers to single, polynuclear, conjugated and fused residues of aromatic hydrocarbons preferably having 6 to 20 carbon atoms, such as phenyl, biphenyl, terphenyl, quaterphenyl, phenoxyphenyl, naphthyl, anthryl and the like.

The term "alkyl" refers to a straight chain, branched, mono- or poly-cyclic saturated hydrocarbon chain, preferably having from 1 to 10 carbon atoms, most preferably 1 to 6 carbon atoms such as methyl, ethyl, n-propyl, isopropyl, n-butyl, secondary butyl, tert-butyl, n-hexyl, n-heptyl, n-octyl, n-decyl, n-dodecyl, 2-ethyldodecyl, tetradecyl, cyclopropyl, cyclobutyl, cyclopentyl, cyclohexyl and the like, unless otherwise indicated. In some instances, the alkyl groups are said to be $C_{1-4}$ alkyl groups. When this term is used either alone or in a compound word such as "optionally substituted $C_{1-4}$ alkoxy", this term refers to straight chained, branched or cyclic hydrocarbon groups having from 1 to 4 carbon atoms. Illustrative of such alkyl groups are methyl, ethyl, propyl, isopropyl, butyl, isobutyl, sec-butyl, cyclopropyl, cyclobutyl and tert-butyl.

The term "alkenyl" refers to a straight chain branched, mono- or poly-cyclic unsaturated hydrocarbon chain, preferably having from 2 to 10 carbon atoms, most preferably 2 to 6 carbon atoms such as vinyl, 1-propenyl, 1- and 2-butenyl, 2-methyl-2-propenyl, 1-pentenyl, 1-hexenyl, 3-hexenyl, 1-heptenyl, 3-heptenyl, 1-octenyl, 1-nonenyl, 2-nonenyl, 3-nonenyl, 1-decenyl, 3-decenyl, 1,3-butadienyl, 1–4,pentadienyl, 1,3-hexadienyl, 1,4-hexadienyl, cyclopentenyl, cyclohexenyl, cycloheptenyl, cyclooctenyl and the like, unless otherwise indicated.

The term "alkynyl" refers to a straight chain, branched, mono- or poly-cyclic unsaturated hydrocarbon chain, preferably having from 2 to 10 carbon atoms, most preferably 2 to 6 carbon atoms such as ethynyl, 1-propynyl, 1- and 2-butynyl, 2-methyl-2-propynyl, 2-pentynyl, 3-pentynyl, 4-pentynyl,2-hexynyl,3-hexynyl,4-hexynyl,5-hexynyl,10-undecynyl,4-ethyl-l-octyn-3-yl, 7-dodecynyl, 9-dodecynyl, 10-dodecynyl, 3-methyl-l-dodecyn-3-yl, 2-tridecynyl, 11-tridecynyl, 3-tetradecynyl, 7-hexadecynyl, 3-octadecynyl and the like, unless otherwise indicated.

The terms "alkylene", "alkenylene" and "alkynylene" are the divalent radical equivalents of the terms "alkyl", "alkenyl" and "alkynyl", respectively. The two bonds connecting the alkylene, alkenylene or alkynylene to the adjacent groups may come from the same carbon atom or different carbon atoms in the divalent radical.

The term "heterocycle" refers to a cyclic alkyl, alkenyl or alkynyl group of from 1 to 40 carbon atoms containing at least one heteroatom selected from oxygen, nitrogen and sulphur. Examples include unsaturated 3 to 6 membered heteromonocyclic groups containing 1 to 4 nitrogen atoms, such as, pyrrolyl, pyrrolinyl, imidazolyl, pyrazolyl, pyridyl, pyrimidinyl, pyrazinyl, pyridazinyl, triazolyl or tetrazolyl;

saturated 3 to 6-membered hetermonocyclic groups containing 1 to 4 nitrogen atoms, such as, pyrrolidinyl, imidazolidinyl, piperidino or piperazinyl;

unsaturated condensed heterocyclic groups containing 1 to 5 nitrogen atoms, such as, indolyl, isoindolyl, indolizinyl, benzimidazolyl, quinolyl, isoquinolyl, indazolyl, benzotriazolyl or tetrazolopyridazinyl;

unsaturated 3 to 6-membered heteromonocyclic group containing an oxygen atom, such as, pyranyl or furyl;

unsaturated 3 to 6-membered hetermonocyclic group containing 1 to 2 sulphur atoms, such as, thienyl;

unsaturated 3 to 6-membered heteromonocyclic group containing 1 to 2 oxygen atoms and 1 to 3 nitrogen atoms, such as, oxazolyl, isoxazolyl or oxadiazolyl;

saturated 3 to 6-membered heteromonocyclic group containing 1 to 2 oxygen atoms and 1 to 3 nitrogen atoms, such as, morpholinyl;

unsaturated condensed heterocyclic group containing 1 to 2 oxygen atoms and 1 to 3 nitrogen atoms, such as, benzoxazolyl or benzoxadiazolyl;

unsaturated 3 to 6-membered heteromonocyclic group containing 1 to 2 sulphur atoms and 1 to 3 nitrogen atoms, such as, thiazolyl or thiadiazolyl;

saturated 3 to 6-membered heteromonocyclic group containing 1 to 2 sulphur atoms and 1 to 3 nitrogen atoms, such as, thiazolidinyl; and unsaturated condensed heterocyclic group containing 1 to 2 sulphur atoms and 1 to 3 nitrogen atoms, such as, benzothiazolyl or benzothiadiazolyl heteroatom selected from oxygen, nitrogen and sulphur.

The term “heteraromatic” refers to any of the unsaturated heterocyclic compounds defined above which are also aromatic.

Suitable substituents include halo, alkyl, alkene, alkyne, aryl, heterocyclic, haloalkyl, haloalkene, haloalkyne, acyl, acyloxy, hydroxy, amino, substituted amino groups such as NHacyl, alkylamino, nitro, thio, alkylthio, carboxy, sulphonic acid, sulphoxides, sulphonamides, quaternary ammonium groups and alkoxy groups such as methoxy, alkenyloxy, alkynyloxy haloalkoxy, haloalkenyloxy, haloalkynyloxy and are preferably F, Cl, hydroxy, $C_{1-6}$alkoxy, $C_{1-6}$alkylamino or carboxy.

Halo will be understood to mean Cl, F, Br or I.

The term “optionally substituted” refers to a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, alkylthio, benzylthio, acylthio, phosphorus-containing groups and the like. In some instances in this specification, where substituents may be present, preferred substituents have been mentioned.

Protecting groups may in general be chosen from any of the groups described in the literature or known to the skilled chemist appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Examples of hydroxyl protecting groups include lower alkyl groups (eg. t-butyl), lower alkenyl groups (eg. allyl); lower alkanoyl groups (eg. acetyl); lower alkoxycarbonyl groups (eg. t-butoxycarbonyl); lower alkenyloxycarbonyl groups (eg. allyloxycarbonyl); aryl lower alkoxycarbonyl groups (eg. benzoyloxycarbonyl, p-methoxybenzyloxycarbonyl, o-nitrobenzyloxycarbonyl, p-nitrobenzyloxycarbonyl); tri(lower alkyl)silyl (eg. trimethylsilyl, t-butyldimethylsilyl) and aryl lower alkyl (eg. benzyl) groups. An acetyl group is preferred.

Methods appropriate for removal of hydroxy protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

The term “morphine-like opioid” is used herein in its broadest sense and refers to any compounds, natural or synthetic, having a morphine-like action. The term encompasses morphine and its natural and semisynthetic derivatives, together with other chemical classes of drugs with pharmacological actions similar to those of morphine. Compounds in these groups have agonistic (including competitive or partial agonistic) activity on at least one of the opiate receptors. Hence, these compounds variably have the capacity to produce analgesia, respiratory depression, gastrointestinal spasm and/or morphine-like physical dependence. Groups of compounds in this class include morphinans (in which the C7 to C8 double bond is a single bond, and optionally the ether oxygen between positions 4 and 5 is removed), the morphinones and dihydromorphinones (in which the OH at C6 is replaced with =O, and optionally the C7 to C8 double bond is a single bond, and also optionally the ether oxygen between C4 and C5 is not present), the Diels-Alder adducts of thebaine (in which there is an endoetheno bridge between C6 and C14, or an endoethano bridge between C6 and C14, and optionally a C7 substitution), benzomorphans (in which the cycloalkene ring and the tetrahydrofuran rings are absent) and phenylpiperidines. Such compounds are well known in the art; see for example “The Pharmacological Basis of Therapeutics” (ed. A. G. Gilman et al; $7^{th}$ edition, 1985, chapter 22). It will be clearly understood that all of the compounds set out in Table 1 of PCT/AU00/00062 are suitable for use in the invention.

The radical form of the morphine-like opioid is constituted by the morphine-like opioid with the atom or group on the nitrogen of the morphine-like opioid removed.

Structurally, the morphine-like opioid radicals include the radicals of formulae II and III defined above.

The radicals encompassed by the structure of Figure II may be divided into a number of groups:

(a) the morphine derivatives in which there is a single double bond between C7 and C8 (or C6 and C8, as in the case of pseudocodeine), and there is no bridging group between C6 and C14;

(b) the morphinan derivatives in which there are no double bonds between any of C6, C7, C8 and C14, and no bridging group between C6 and C14, (including one subclass in which $R^b$ is H, and another in which $R^b$ is $=CH_2$);

(c) the morphinone derivatives, in which $R^b$ is =O, and there is no bridging group between C6 and C14 (including the subclass of dihydromorphinones, in which there are also no double bonds between any of C6, C7, C8 and C14); and (d) the thebaine derivatives (Diels-Alder adducts of thebaine), in which there is an endoetheno or an endoethano bridge between C6 and C14 (including the particularly important subclass where $R^e$ is (figure)).

The radicals encompassed by the structure of FIG. III may be divided into a number of groups including:

(e) the benzomorphan derivatives, in which the bonds represented by the broken lines are present; and (f) the phenylpiperidines, in which the bonds represented by the broken lines are not present (including the significant subclass in which $R^i$ is $C_{1-4}$ alkanoyl).

For the synthesis of the compounds of formula I, the precursors for radical components are utilised. A precursor for a radical is either:

a compound containing the radical coupled to a functional group that is removed during reaction to couple the radical to another radical; or a compound from which the radical is formed by chemical rearrangement during the reaction, with removal of an atom or group from the compound.

For the first type of precursor, suitable functional groups depend on the reaction being conducted, and may for instance be hydrogen, an amine, halogen, alcohol, and so forth.

It will be appreciated by those skilled in the art that the compounds of formula I may be modified to provide pharmaceutically acceptable derivatives thereof at any of the functional groups in the compounds of formula I. Of particular interest as such derivatives are compounds modified at the carboxyl function, hydroxyl functions or at the guanidino or amino groups. Thus compounds of interest include $C_{1-6}$alkyl esters, such as methyl, ethyl, propyl or isopropyl esters, aryl esters, such as phenyl, benzoyl esters, and $C_{1-6}$acetyl esters of the compounds of formula I. Consequently, the term "pharmaceutically acceptable derivative" means any pharmaceutically acceptable salt, ester or salt of such ester of a compound of formula I or any other compound which, upon administration to the recipient, is capable of providing (directly or indirectly) a compound of formula I or a biologically active metabolite or residue thereof.

Pharmaceutically acceptable salts of the compounds of formula I include those derived from pharmaceutically acceptable cations, inorganic and organic acids and bases. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicylic, sulphanilic, aspartic, glutamic, edetic, stearic, palmitic, oleic, lauric, pantothenic, tannic, ascorbic and valeric acids. Some of the acids mentioned above such as oxalic acid, while not in themselves pharmaceutically acceptable, may be useful in the preparation of salts useful as intermediates in obtaining compounds of the invention and their pharmaceutically acceptable acid addition salts.

The term "pro-drug" is used herein in its broadest sense to include those compounds which are converted in vivo to compounds of Formula I.

The term "tautomer" is used herein in its broadest sense to include compounds of Formula I which are capable of existing in a state of equilibrium between two isomeric forms. Such compounds may differ in the bond connecting two atoms or groups and the position of these atoms or groups in the compound.

The term "isomer" is used herein in its broadest sense and includes structural, geometric and stereo isomers. As the compound of Formula I have one or more chiral centres, it is capable of existing in enantiomeric forms.

Some compounds of the invention are optically active, and it will be clearly understood that both racemic mixtures and isolated stereoisomers are within the scope of the invention. A method of separating enantiomers of mianserin-like compounds with a guanidino-type substituent is disclosed in our International patent application No.PCT/AU98/00807 (WO99/16769), and could be used with the compounds of the invention. Other methods of resolution for amino compounds are summarised in Chapter 7, Separation of Stereoisomers. Resolution. Racemisation, pages 297–421 of E. L. Eliel, S. H. Wilen and L. N. Mander, Stereochemisty of Organic Compounds, Wiley-Interscience, New York, 1994.

The compositions of the present invention comprise at least one compound of Formula I together with one or more pharmaceutically acceptable carriers and optionally other therapeutic agents. Each carrier, diluent, adjuvant and/or excipient must be pharmaceutically "acceptable" in the sense of being compatible with the other ingredients of the composition and not injurious to the subject. Compositions include those suitable for oral, rectal, nasal, topical (including buccal and sublingual), vaginal or parenteral (including subcutaneous, intramuscular, intravenous and intradermal) administration. The compositions may conveniently be presented in unit dosage form and may be prepared by methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers, diluents, adjuvants and/or excipients or finely divided solid carriers or both, and then if necessary shaping the product.

The compounds of the present invention may be used to treat a condition or symptom that is inhibited, reduced or alleviated by opioid receptor activation. This refers to conditions or symptoms that are associated with one or more of the nervous system, vascular system, gastointestinal system, pulmonary system and heart. Examples of such conditions are pain, pulmonary edema and diarrhoea.

It will be understood that the brain and spinal cord are CNS organs which lie principally inside (central to) the blood brain barrier. Accordingly, an agent with "reduced or no CNS activity" will act primarily with cells or tissues of the body which lie outside (peripheral to) the blood brain barrier. The specificity for "reduced or no CNS activity" may be a result of the inhibition of the passage of the agent from the circulation across the blood brain barrier into the CNS.

The term "subject" as used herein refers to any animal having a disease or condition which requires treatment with a pharmaceutically-active agent. The subject may be a mammal, preferably a human, or may be a domestic or companion animal. While it is particularly contemplated that the compounds of the invention are suitable for use in medical treatment of humans, it is also applicable to veterinary treatment, including treatment of companion animals such as dogs and cats, and domestic animals such as horses, ponies, donkeys, mules, llama, alpaca, pigs, cattle and sheep, or zoo animals such as primates, felids, canids, bovids, and ungulates.

Suitable mammals include members of the Orders Primates, Rodentia, Lagomorpha, Cetacea, Carnivora, Perissodactyla and Artiodactyla. Members of the Orders Perissodactyla and Artiodactyla are particularly preferred because of their similar biology and economic importance.

For example, Artiodactyla comprises approximately 150 living species distributed through nine families: pigs (Suidae), peccaries (Tayassuidae), hippopotamuses (Hippopotamidae), camels (Camelidae), chevrotains (Tragulidae), giraffes and okapi (Giraffidae), deer (Cervidae), pronghorn (Antilocapridae), and cattle, sheep, goats and antelope (Bovidae). Many of these animals are used as feed animals in various countries. More importantly, many of the economically important animals such as goats, sheep, cattle and pigs have very similar biology and share high degrees of genomic homology.

The Order Perissodactyla comprises horses and donkeys, which are both economically important and closely related. Indeed, it is well known that horses and donkeys interbreed.

As used herein, the term "therapeutically effective amount" is meant an amount of a compound of the present invention effective to yield a desired therapeutic response, for example, to induce analgesia.

The specific "therapeutically effective amount" will, obviously, vary with such factors as the particular condition being treated, the physical condition of the subject, the type of subject being treated, the duration of the treatment, the nature of concurrent therapy (if any), and the specific formulations employed and the structure of the compound or its derivatives.

The compounds of the present invention may additionally be combined with other medicaments to provide an operative combination. It is intended to include any chemically compatible combination of pharmaceutically-active agents, as long as the combination does not eliminate the activity of the compound of formula I. It will be appreciated that the compound of the invention and the other medicament may be administered separately, sequentially or simultaneously.

Methods and pharmaceutical carriers for preparation of pharmaceutical compositions are well known in the art, as set out in textbooks such as Remington's Pharmaceutical Sciences, 20th Edition, Williams & Wilkins, Pennsylvania, USA.

As used herein, a "pharmaceutical carrier" is a pharmaceutically acceptable solvent, suspending agent or vehicle for delivering the compound of formula I to the subject. The carrier may be liquid or solid and is selected with the planned manner of administration in mind. Each carrier must be pharmaceutically "acceptable" in the sense of being compatible with other ingredients of the composition and non injurious to the subject.

The compound of formula I may be administered orally, topically, or parenterally in dosage unit formulations containing conventional non-toxic pharmaceutically acceptable carriers, adjuvants, and vehicles. The term parenteral as used herein includes subcutaneous injections, aerosol for administration to lungs or nasal cavity, intravenous, intramuscular, intrathecal, intracranial, injection or infusion techniques.

The present invention also provides suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable preservatives include sodium benzoate, vitamin E, alphatocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate. The tablets contain the active ingredient in admixture with non-toxic pharmaceutically acceptable excipients which are suitable for the manufacture of tablets.

These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

The compound of formula I as well as the pharmaceutically-active agent useful in the method of the invention can be administered, for in vivo application, parenterally by injection or by gradual perfusion over time independently or together. Administration may be intravenously, intraarterial, intraperitoneally, intramuscularly, subcutaneously, intracavity, transdermally or infusion by, for example, osmotic pump. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, growth factors and inert gases and the like.

Generally, the terms "treating", "treatment" and the like are used herein to mean affecting a subject or tissue to obtain a desired pharmacologic and/or physiologic effect. The effect may be the alteration of the perception of nociceptive stimuli. The effect may be prophylactic in terms of completely or partially preventing a sensation, condition, symptom or disease, and/or may be therapeutic in terms of a partial or complete removal of a sensation, condition or symptom, or cure of a disease. In the context of analgesia, the term "treating" covers the treatment of, or prevention of, the sensation of pain. "Treating" as used herein in any other context covers any treatment of, or prevention of, condition, symptom or disease in a vertebrate, a mammal, particularly a human, and includes: (a) preventing the condition, symptom or disease from occurring in a subject that may be predisposed to the condition, symptom or disease, but has not yet been diagnosed as having it; (b) inhibiting the disease, i.e., arresting its development; or (c) relieving or ameliorating the effects of the disease, i.e., cause regression of the effects of the disease.

The invention includes various pharmaceutical compositions useful for ameliorating a sensation (such as pain) or disease. The pharmaceutical compositions according to one embodiment of the invention are prepared by bringing a compound of formula I, analogues, derivatives or salts thereof, or combinations of compound of formula I and one or more pharmaceutically-active agents into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 20th ed. Williams and Wilkins (2000) and The British National Formulary 43rd ed. (British Medical Association and Royal Pharmaceutical Society of Great Britain, 2002; the contents of which are hereby incorporated by reference. The pH and exact concentration of the various components of the pharmaceutical composition are adjusted according to routine skills in the art. See Goodman and Gilman's The Pharmacological Basis for Therapeutics (7th ed., 1985).

The pharmaceutical compositions are preferably prepared and administered in dose units. Solid dose units may be tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of the cytotoxic side effects. Various considerations are described, e.g., in Langer, Science, 249: 1527, (1990). Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono-or diglycerides. In addition, fatty acids such as oleic acid find use in the preparation of injectables.

Compounds of formula I may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula I may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced in the udder via the teat;

(c) topical applications, e.g. as a cream, ointment or spray applied to the skin; or (d) intravaginally, e.g. as a pessary, cream or foam.

Dosage levels of the compound of formula I of the present invention are of the order of about 0.5 mg to about 20 mg per kilogram body weight, with a preferred dosage range between about 0.5 mg to about 10 mg per kilogram body weight per day (from about 5 mg to about 3 g per patient per day, but in the case of palliative care patients about 5 g to about 10 g per patient per day). The amount of active ingredient that may be combined with the carrier materials to produce a single dosage will vary depending upon the host treated and the particular mode of administration. For example, a formulation intended for oral administration to humans may contain about 5 mg to 1 g of an active compound with an appropriate and convenient amount of carrier material which may vary from about 5 to 95 percent of the total composition. Dosage unit forms will generally contain between from about 5 mg to 500 mg of active ingredient.

Optionally the compounds of the invention are administered in a divided dose schedule, such that there are at least two administrations in total in the schedule. Administrations are given preferably at least every two hours for up to four hours or longer; for example the compound may be administered every hour or every half hour. In one preferred embodiment, the divided-dose regimen comprises a second administration of the compound of the invention after an interval from the first administration sufficiently long that the level of active compound in the blood has decreased to approximately from 5–30% of the maximum plasma level reached after the first administration, so as to maintain an effective content of active agent in the blood. Optionally one or more subsequent administrations may be given at a corresponding interval from each preceding administration, preferably when the plasma level has decreased to approximately from 10–50% of the immediately-preceding maximum.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLES

The invention will now be described in detail by way of reference only to the following non-limiting examples and drawings.

Example 1

Preparation of Precursors YN—X—$NH_2$ where X is Straight Chain Alkyl

Methods of synthesis of amine precursors of compounds containing a straight-chained alkyl group as the spacer group "X" are disclosed in PCT/AU00/00062, the full disclosure of which is incorporated into this document by reference. One example is provided below.

Example 1a

Preparation of 3,6-bis(t-butyldimethylsiloxy)-7,8-didehydro-4,5-epoxy-17-(2-cyanoethyl)morphinan Ref: J. A. Bell and C. Kenworthy, Synthesis, 650–652, 1971.

3,6-Bis(t-butyldimethylsiloxy)-7,8-didehydro-4,5-epoxymorphinan (0.26 g, 0.52 mmol) was dissolved in absolute ethanol (3 mL) and acrylonitrile (0.07 ml, 1.0 mmol) was added dropwise at room temperature. The reaction mixture was stirred at room temperature overnight, and the solvent was evaporated under reduced pressure to give a white solid (0.26 g, 90% yield).

Example 1b

Synthesis of (5α,6α)-7,8-didehydro-4,5-epoxy-17-(N-aminoiminomethylaminopropyl)morphinan-3,6-diol (KRS-2-47)

Preparation of 3,6-bis(t-butyldimethylsiloxy)-7,8-didehydro-4,5-epoxy-17-(aminopropylmorphinan)

A solution of 3,6-bis(t-butyldimethylsiloxy)-7,8-didehydro-4,5-epoxy-17-cyanoethylmorphinan (200 mg, 0.36 mmol) in dry ethyl ether (5 ml) was added dropwise to a suspension of lithium aluminum hydride (0.13 g, 3.6 mmol) in dry ethyl ether (5 ml). After stirring for 3 h at room temperature the reaction mixture was added wet ether followed by 10% sodium hydroxide (1.5 ml). The solution was filtered, and the white precipitate was washed with ether. The ether layer was evaporated under reduced pressure to give the amine as a clear liquid (yield=0.2 g, 99%).

Example 2

Preparation of Precursors YN—X—$NH_2$ where X is Branched Chain Alkyl

Examples 1a and 1b are repeated using the following readily available compounds in place of acrylonitrile, to yield the corresponding amine precursor YN—X—$NH_2$ in which X is the corresponding branched chain alkyl.

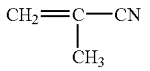

methacrylonitrile

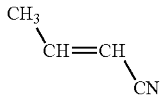

crotononitrile

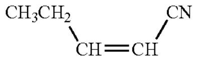

cis-pent-2-ene nitrile

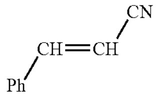

3-phenylacrylonitrile

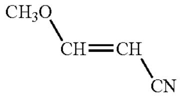

methoxy acrylonitrile

Example 3

Preparation of Precursors YN—X—$NH_2$ where X is Branched Chain Alkyl

As an alternative to Example 2, precursors YN—X—$NH_2$ are prepared by reaction of the demethylated opioid with α-aminoacids yielding an amide, which can be reduced to an amine containing a branch chain with one carbon atom in the spacer. A wide variety of α-aminoacids are commercially available.

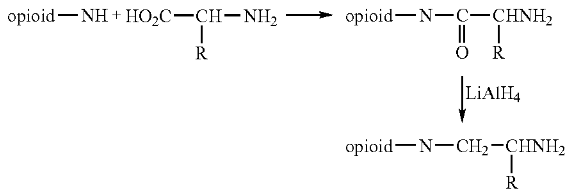

As another alternative to Example 2, β-aminoacids (eg. 3-aminobutanoic acid) are used to produce compounds with a branched chain group with three carbon atoms in the main chain.

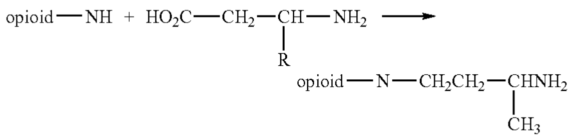

Example 4

Preparation of Precursors YN—X—$NH_2$ where X is Alkenylene

The method disclosed in Albeck, A. et al, *Tetrahedron,* 2000, 56, 1505–1516, is used to prepare the compound containing the protected amino group at one end and hydroxy group at the other end illustrated in the scheme set out below. This compound is then brominated (step 1) using the method and conditions specified in D. Poirier et al, Tet. Lett., Vol 35, 7, 1051, 1995. The brominated product is reacted with the opioid using the conditions and methods set out in one of the following three references:

1. NaOH/isopropanol—Limanov, V. E., Myazina, N. Y. Zh, Prikl Khim. 1988, 61(10), 2365–8.
2. KOH/triethyl amine—Mohri, K. Suzuki, K, Usui N, Isobe, K, Tsuda, Y. Chemical & Pharmaceutical Bulletin 1995, 43 (1), 159–61.
3. CSOH—Salvatore, R. Nagle, A. Schmidt, S. Jung, K. Organic Letters, 1999, 1(12), 1893–96.

Thereafter, the amine is deprotected following the method and conditions outlined in Albeck et al, to yield YN—X—$NH_2$ in which X is an alkenylene.

Example 5

Preparation of Monoarylsubstituted Compounds of Formula I from Precursors YN—X—$NH_2$ or YN—H

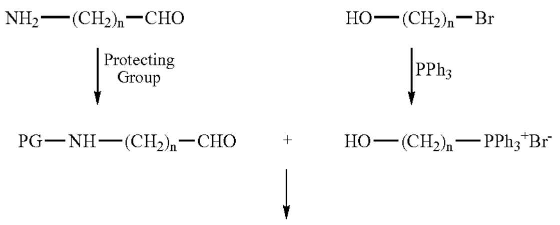

-continued

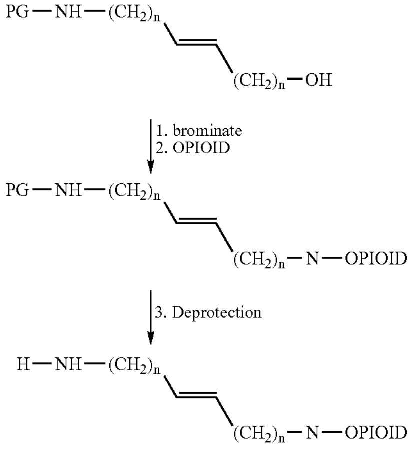

Monoaryl substituted guanidines can be synthesised by a variety of techniques from the amines outlined above.

Monoarylsubstituted guanidines can be made by different methods, for example (a) Reaction of the corresponding amine (YN—X—$NH_2$ or YN—H, eg YN—$(CH_2)_n$—$NH_2$) with a sulfonic acid of a monosubstituted thiourea.

The sulfonic acid is prepared by reacting the thiourea with an oxidising agent, such as $H_2O_2/NaMoO_4$ (Maryanoff et al, 1986).

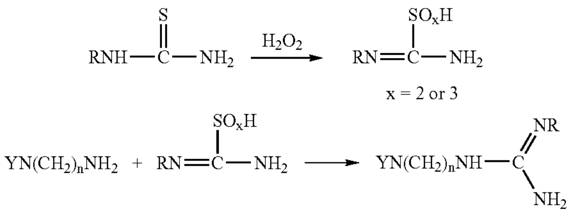

R being as defined in Formula I (b) Reacting the amine with cyanogen bromide to give a cyanamide, and then reacting the cyanamide with an appropriate amine ($R'NH_2$)). (Reddy L. N. et al 1994)

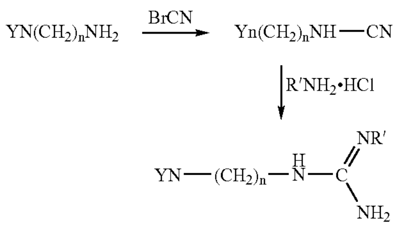

Example 6

Preparation of Diarylsubstituted Compounds of Formula I

Diaryl substituted guanidines can be synthesised from the corresponding amine YN—X—$NH_2$ by reacting with a carbodiimide. Carbodiimides are prepared from the corresponding urea by reaction with a dehydration agent such as Burgess reagent (Barvian et al, 1997)or triphenylphosphine dibromide (Palomo et al, 1981) as shown in reaction scheme (i) below. Carbodiimides can also be prepared from the reaction of isocyanates with commercially available N-(triphenylphosphoranylidene)aniline as shown in reaction scheme (ii) below. Some carbodiimides are also commercially available. There may be a wide range of substituents on the phenyl groups, and R and R' may be the same or different.

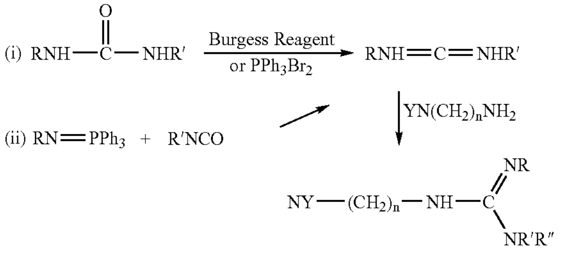

(b) Disubstituted guanidines can be synthesised by the reaction of the amine with an oxidised diarylthiourea. Diarylthiourea can be oxidised using oxidising agents such as benzyltriethyl ammonium permanganate (Ramadas et al, 2001).

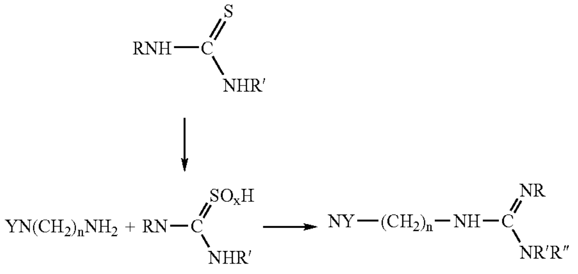

(x = 2 or 3)

Example 7

Preparation of Tri-aryl Substituted Compounds of Formula I

Tri-aryl substituted compounds of Formula I are prepared from a carboximidamide precursor containing the three aryl groups. The carboximidamide precursor is in one or both of its isomeric forms, and is synthesised using the method and conditions set out in Katritzky, A. R. et al, *J Org Chem,* 2001, 66, 2854–2857. These methods for the synthesis of the benzotriazole-1-carboximidamide are incorporated herein by reference.

The compound YN—H or YN—X—$NH_2$ prepared by one of the methods outlined above is reacted with the benzotriazole-1-carboximidamide containing R, R' and R" to yield the compound of formula I.

Example 8

Preparation of Compounds of Formula I from Precursors for the Radical —X—$(NH)_{0\ or\ 1}$—C(=NR)—NR'R"

Particularly in the context of including a heteroatom such as oxygen in the group X, the compounds of Formula I may be synthesised from the precursors for the radical —X—$(NH)_{0\ or\ 1}$—C(=NR)—NR'R".

For the formation of an ether in the group X, the compounds of Formula I are prepared using the following reaction scheme.

The addition of the guanidine functionality involves the use of one of the general procedures outlined above in Examples 5, 6 and 7, with the modification that the amine used will be the amine outlined in the following scheme, and not the opioid-containing amine. In all other respects, the reactions remain the same.

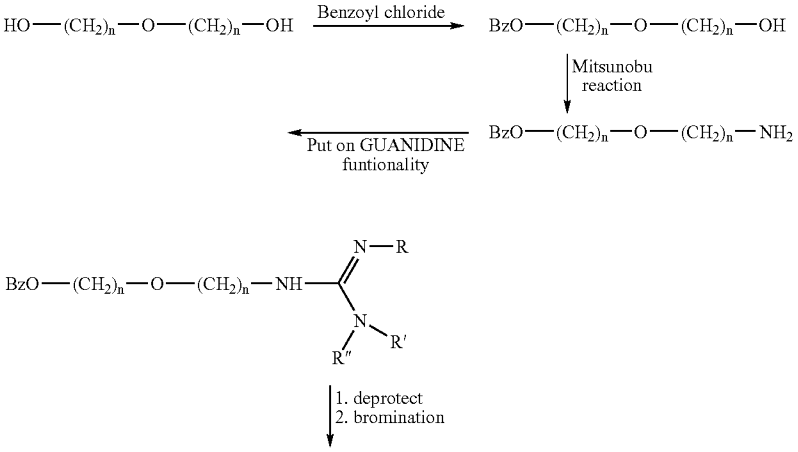

-continued

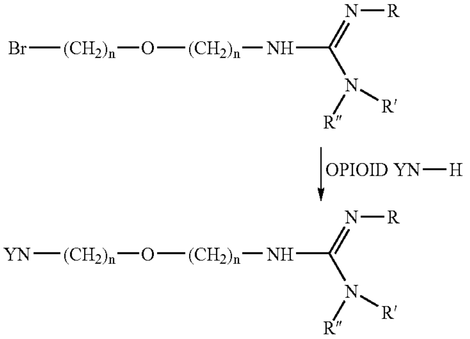

Example 9

Synthesis of (5α,6α)-7,8 didehydro-4,5-epoxy-17-(N,N'-bisphenyl carboxamidino-3-aminopropyl) morphinan,3,6-diol (KRS-5-150)

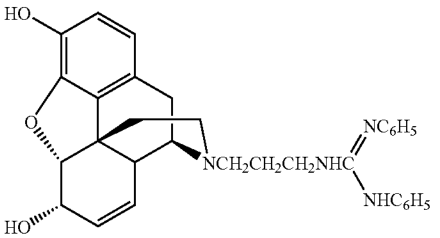

KRS-5-150

Reaction Scheme for the Synthesis of KRS-5-150

Preparation of 6(t-butyldimethylsiloxy)-7,8-didehydro-4,5-epoxy-17-(N,N'-bisphenylcarboxamidino-3-aminopropyl) morphinan-3-ol N,N'-bis(phenyl)carbodiimide was prepared according to the method of Barvian et al (1997), and was used without further purification). 3,6-bis(t-butyldimethylsiloxy)-7,8-didehydro-4,5-epoxy-17-(3-aminopropyl)morphinan (187 mg, 0.336 mmol) was added to a stirred suspension of NaH (60% in oil, 0.016 g, 0.403 mmol) in anhydrous DMF (2 ml), under nitrogen atmosphere. After stirring for 10 minutes, a solution of N,N'-bis(phenyl)carbodiimide (97.7 mg, 0.504 mmol) in DMF (2 ml) was added dropwise over 10 minute period. After stirring for 4 hours at room temperature, the reaction mixture was diluted with aqueous ammonium chloride (15 ml) and extracted with methylene chloride. The methylene chloride layer was dried over sodium sulphate and concentrated. The crude concentrate was chromatographed on silica gel using methylene chloride/methanol/ammonium hydroxide 9:2:0.2 to give the guanidine as a white solid. (yield=104 mg, 48%).

Preparation of (5α,6α)-7,8 didehydro-4,5-epoxy-17-(N,N'-bisphenyl carboxamidino-3-aminopropyl)morphinan,3,6-diol (KRS-5-150).

6-(t-butyldimethylsiloxy)-7,8-didehydro-4,5-epoxy-17-(N,N'-bisphenylcarboxamidino-3-aminopropyl)morphinan-3-ol was deprotected using 0.05 ml of 48% HF in 10:2 acetonitrile and tetrahydrofuran. The reaction mixture was evaporated and the white solid was chromatographed on silica gel using methylene chloride/methanol/ammonium hydroxide 9:2:0.2. KRS-5-150 was obtained as a white powder (yield=78%) M.p. 130–132° C.

Example 10

Synthesis of 17-(N,N'-bisphenylcarboxamidino-3-aminopropyl)-7α-(1-hydroxy-1-methylethyl)-6,14-endo-ethanotetrahydronororipavine (KRS-6-79)

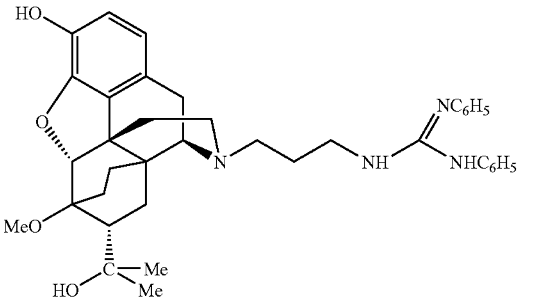

KRS-6-79

Preparation of 3-(t-butyldimethylsiloxy)-17-(N,N'-bisphenylcarboxamidino-3-aminopropyl)-7α-(1-hydroxy-1-methylethyl)-6,14-endo-ethanotetrahydronororipavine N,N'-bisphenyl carbodiimide was prepared from 1,3 diphenyl urea by reacting with bromotriphenylphosphonium bromide and triethylamine in dichloromethane. Bromotriphenylphosphonium bromide was made in situ by adding bromine to a solution of triphenyl phosphine in dichloromethane at 0° C. Ref. Palomo, C. Mestres, R. Synthesis 373, 1981

3-(t-butyldimethylsiloxy)-17-aminopropyl-7α-(1-hydroxy-1-methylethyl)-6,14-endo-ethanotetrahydronororipavine (250 mg, 0.461 mmol) in anhydrous dimethyl formamide (2 mL) was added N,N'-bisphenyl carbodiimide (0.134 g, 0.691 mmol) in 2 mL dimethylformamide and the reaction mixture was stirred overnight at room temperature. Dimethylformamide was removed under reduced pressure and the crude product was chromatographed on silica gel using dichloromethane/methanol/ammonium hydroxide in 9:1:0.1 ratio to give the guanidine as a white solid (230 mg, 68% yield).

Preparation of 17-(N,N'-bisphenylcarboxamidino-3-aminopropyl)-7α-(1-hydroxy-1-methylethyl)-6,14-endo-ethanotetrahydronororipavine (KRS-6-79)

3-(t-butyldimethylsiloxy)-17-(N,N'-bisphenylcarboxamidino-3-aminopropyl)-7α-(1-hydroxy-1-methylethyl)-6,14-endo-ethanotetrahydronororipavine (220 mg, 0.3 mmol) in methanol was added ammonium fluoride (0.12 g, 3.125 mmol) and stirred overnight at room temperature. The solvents were evaporated and the crude was chromatographed on silica gel using dichloromethane/methanol/ammonium hydroxide in 9:1:0.1 ratio to give KRS-6-79 as a white solid (0.181 g, 96% yield).

Example 11

Synthesis of (5α,6α)-7,8-didehydro-4,5-epoxy-17-(N,N'-bis-p-tolylcarboxamidino-3-aminopropyl)morphinan-3,6-diol (KRS-6-26)

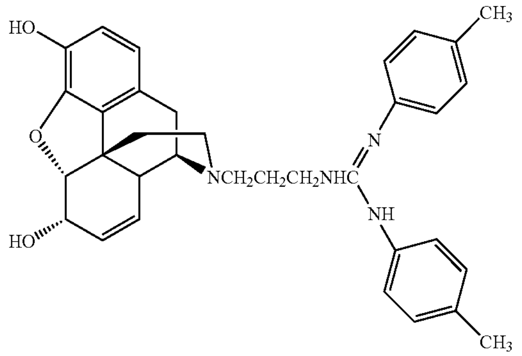

KRS-6-26

Preparation of (5α,6α)-7,8-didehydro-4,5-epoxy-17-(N,N'-bis-p-tolylcarboxamidino-3-aminopropyl)morphinan-3,6-diol (KRS-6-26).

3,6-bis(t-butyldimethylsiloxy)-7,8-didehydro-4,5-epoxy-17-(N-3-aminopropyl)morphinan (223 mg, 0.4 mmol) was added to a stirred suspension of NaH (60% in oil, 0.0176 g, 0.44 mmol) in andydrous DMF (2 mL), under nitrogen atmosphere. After stirring for 10 minutes, a solution of N,N'-bis-p-tolylcarbodimide (0.092 mg, 0.4 mmol) in DMF (2 mL) was added dropwise. After stirring for 3 hours at room temperature, the reaction mixture was diluted with aq. ammonium chloride (25 mL) and extracted with methylene chloride. The methylene chloride layer was dried and the crude was chromatographed on silica gel using methylene chloride/methanol/ammonium hydroxide 9:2:0.2 to give a mixture of disilyl protected and monosilyl protected guanidines 56 mg (0.072 mmol) and 43 mg (0.064 mmol) respectively (33% yield).

The mixture of protected guanidines were deprotected using 48% HF in 10:2 acetinitrile and tetrahydrofuran. The crude was chromatographed on silica gel using methylene chloride/methanol/ammonium hydroxide in 9:1:0.1 ratio to give KRS-6-26 as a white solid (65 mg, 86% yield). M. p. 128–130° C.

Example 12

Synthesis of 3,6-bis(t-butyldimethylsiloxy)-7,8-didehydro-4,5-epoxy-17-(N,N'-bisphenylcarboxamidino)morphinan(JFY-050)

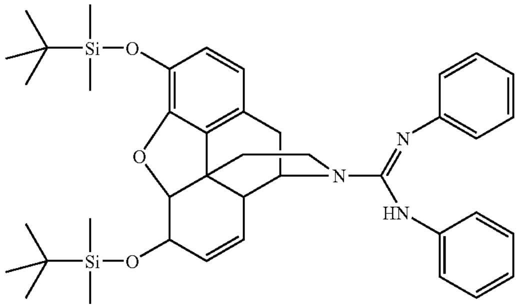

JFY-050

3,6-Bis(t-butyldimethylsiloxy)-7,8-didehydro-4,5-epoxymorphinan (250 mg, 0.5176 mmol) was dissolved in 2 ml anhydrous DMF and placed under nitrogen to stir. The diphenyl carbodiimide (150 mg, 0.7764 mmol) was dissolved in 1 ml anhydrous DMF and added slowly to the stirring solution, resulting in a yellow solution. This was left to stir for 5 hrs at room temperature before slowly adding 5.2 ml of saturated ammonium chloride solution. The product was extracted with dichloromethane before drying over anhydrous sodium sulphate and solvent removed under reduced pressure. The product was dried for a further 4 hrs on the vacuum pump and a yellow-orange, viscous oil obtained. This was purified by several columns, firstly using 90:10:1 dichloromethane:MeOH:$NH_4OH$ solution as the eluent, then solutions of ethyl acetate:hexane, 1:1 then 4:1. The product obtained was a clear oil. (0.3031 g, 86%).

Example 13

Synthesis of (5α,6α)-7,8-didehydro-4,5-epoxy-17-(N,N'-bisphenylcarboxamidino)morphinan, 3,6-diol (JFY-058)

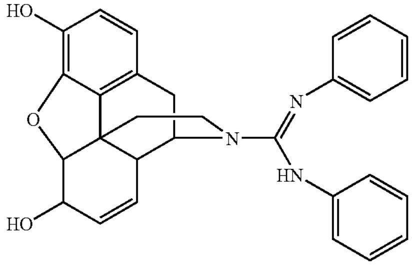

JFY-058

3,6-bis(t-butyldimethylsiloxy)-7,8-didehydro-4,5-epoxy-17-(N,N'-bisphenylcarboxamidino)morphinan (0.1739 g, 0.251 mmol) was dissolved in 5 ml methanol and placed under nitrogen to stir for ten minutes. $NH_4F$ was then added to the solution then left to stir overnight at room temperature under nitrogen. The reaction was ceased after 18.5 hrs and solvent removed under reduced pressure. The resulting solid was partially dissolved in a small amount of 90:10:1 $CH_2Cl_2$:MeOH:$NH_4OH$ solution and transferred into a small silica column to be run in the same eluent. This column was repeated with the product, perhaps a step that could be avoided if a larger column was used. The solvent was again removed under reduced pressure to afford a fine white powder (0.1475 g, 182° C., 73%).

Example 14

Synthesis of (5α,6α)-7,8-didehydro-4,5-epoxy-17-(N,N'-bis-p-tolyl-carboxamidino)morphinan-3,6-diol (KRS-6-85)

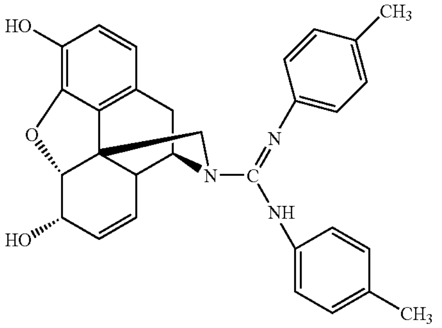

KRS-6-85

A suspension of 1,3-di-p-tolylcarbodiimide (0.122 g, 0.55 mmol) in anhydrous dimethylformamide was added to a solution of 3,6-bis(t-butyldimethylsiloxy)-7,8-didehydro-4,5-epoxy-17-(3-aminopropyl)morphinan (250 mg, 0.5 mmol) in anhydrous dimethylformamide (2 ml). After stirring overnight at room temperature under nitrogen atmosphere, dimethylformamide was removed under reduced pressure. The crude product was chromatographed on silica gel using 1:1 mixture of ethyl acetate and haxane to give 3,6-bis-(t-butyldimethylsiloxy)-7,8-didehydro-4,5-epoxy-17-(N,N'-bis-p-tolylcarboxamidino)morphinan as a thick colourless liquid (0.356 g, 0.504 mmol). This was deprotected using 10 equivalents of ammonium fluoride in methanol. The crude product was chromatographed on silica gel using dichloromethane/methanol/ammonium hydroxide in 9:1:0.1 ratio to give KRS-6-85 as a white solid. (0.247 g, 0.5 mmol, 93% yield). M.p. 156–158° C.

Example 15

Synthesis of (5α,6α)-7,8 didehydro-4,5-epoxy-17-(N-phenyl carboxamidino-3-aminopropyl)morphinan-3,6-diol (KRS-6-22)

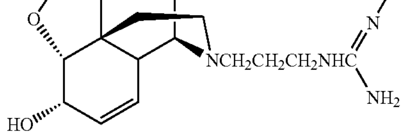

KRS-6-22

Preparation of 3,6-bis (t-butyldimethylsiloxy)-7,8-didehydro-4,5-epoxy-17-(N-phenylcarboxamidino-3-aminopropyl)morphinan 3,6-bis(t-butyldimethylsiloxy)-7,8-didehydro-4,5-epoxy-17-(3-aminopropyl)morphinan (137 mg, 0.246 mmol) in a mixture of acetonitrile (1 ml) and tetrahydrofuran (2 ml) was added to N-phenylaminoiminomethanesulfonic acid (0.05 g, 0.246 mmol). After stirring overnight at room temperature, the pH was adjusted to 12 with 1N NaOH. The solvents were evaporated and 10 ml water was added and then extracted with dichloromethane. The organic layer was dried and evaporated to give the crude product. The crude was purified by column chromatography on silica gel using dichloromethane/methanol/ammonium hydroxide in 9:2:0.2 and then 4:2:2 to give the guanidine as a white solid (119 mg, 0.176 mmol, 77% yield).

N-phenylaminoiminomethanesulfonic acid was prepared according to Maryanoff, C. A. et al, J. Org. Chem. 1986, 51, 1882–1884.

Preparation of (5α,6α)-7,8 didehydro-4,5-epoxy-17-(N-phenyl carboxamidino-3-aminopropyl)morphinan-3,6-diol (KRS-6-22)

3,6-bis (t-butyldimethylsiloxy)-7,8-didehydro-4,5-epoxy-17-(N-phenylcarboxamidino-3-aminopropyl)morphinan was deprotected using 10 equivalents of 48% HF in 4:1 acetonitrile and tetrahydrofuran. The reaction mixture was evaporated to dryness and the crude product was chromatographed on silica gel using methylene chloride/methanol/ammonium hydroxide in 9:2:0.2 ratio. KRS-6-22 was obtained as a white solid (81 mg, 94%. M.p. 128° C.

Example 16

Analgesic Activity of KRS-5-150

KRS-5-150 was evaluated for possible analgesic activity in the phenylquinone-induced writhing model in mice (Siegmund et al, 1957). A serial 2-fold dosage variance was used in the test, from 128 mg/kg to 1 mg/kg (8 doses in total). Groups of 3 male or female ICR mice weighing 22±2 g were employed. A serial 2-fold dosage variance was used in the test (8 doses in total). Variant doses (1, 2, 4, 8, 16, 32, 64 and 128 mg/kg) of test substances were administered intraperitoneally (IP). A vehicle of 2% Tween 80 in 0.9% NaCl was used for the intraperitoneal injection. The control group received vehicle alone. Phenylquinone (PQ) at dose of 2 mg/kg was injected intraperitoneally 30 minutes (IP) after test substance, and the number of writhes exhibited during the following 5–10 minute period was recorded. A reduction in the number of writhes by 50 percent or more (≧50%) relative to the vehicle-treated group indicated possible analgesic activity.

KRS-5-150

Significant activity was found for KRS-5-150 at doses of 64, 32, 16, 8, 4 and 2 mg/kg. These results are summarised in Table 1. KRS-5-150 did not exhibit Straub tail behaviour at these doses. The Straub test is an indicator of CNS activity. In contrast to this finding, in response to morphine at 3 mg/kg, 1 of 3 test animals exhibited the Straub tail phenomenon. This indicates that KRS-5-150 is able to exert an analgesic effect without a central effect on the central nervous system.

TABLE 1

Analgesia in the Phenylquinone Writhing Model

| Treatment | Route | Dose | N | No. of Writhings Individual | Average | % Inhibition |
|---|---|---|---|---|---|---|
| Vehicle | IP | 20 ml/kg | 1 | 19 | | |
| (2% Tween | | | 2 | 9 | | |
| 80/0.9% NaCl) | | | 3 | 17 | 15 | — |
| (KRS-5-150) | IP | 1 mg/kg | 1 | 16 | | |
| | | | 2 | 14 | | |
| | | | 3 | 0 | 10 | 33 |
| | IP | 2 mg/kg | 1 | 8 | | |
| | | | 2 | 1 | | |
| | | | 3 | 4 | 4 | 73 |
| | IP | 4 mg/kg | 1 | 0 | | |
| | | | 2 | 7 | | |
| | | | 3 | 3 | 3 | 80 |
| | IP | 8 mg/kg | 1 | 4 | | |
| | | | 2 | 0 | | |
| | | | 3 | 2 | 2 | 87 |
| | IP | 16 mg/kg | 1 | 0 | | |
| | | | 2 | 4 | | |
| | | | 3 | 5 | 3 | 80 |
| | IP | 32 mg/kg | 1 | 0 | | |
| | | | 2 | 0 | | |
| | | | 3 | 1 | 0 | 100 |
| | IP | 64 mg/kg | 1 | 0 | | |
| | | | 2 | 0 | | |
| | | | 3 | 0 | 0 | 100 |
| | IP | 128 mg/kg | 1 | 0 | | 2/3 died |
| | | | 2 | | | |
| | | | 3 | | | |
| Morphine.HCl | IP | 3 mg/kg | 1 | 0 | | |
| | | | 2 | 0 | | |
| | | | 3 | 0 | | 100 |

Example 17

Further Investigation of Analgesic Activity of KRS-5-150

Further testing on compound KRS-5–150 was carried out under contract by MDS Pharma Services—Taiwan Ltd. The study was designed to evaluate the effects of the compound as an analgesic in the phenylquinone-induced writhing assay, which was described in the previous example, and in the radiant heat-induced tail-flick response assay in mice (D'Amour et al., 1941).

For the phenylquinone writhing test, groups of three male or female ICR-derived mice weighing 22±2 g were used. For the phenylquinone writhing test, KRS-5-150 at doses of 1, 2, 4, 8, 16, 32, 64 and 128 mg/kg in either 2% Tween 80/0.9% NaCl or in 2% Tween 80 was used for intraperitoneal administration, or at doses of 1, 2, 4, 8, 16, 32 or 64 mg/kg in the same vehicles for oral administration. Control animals received vehicle alone. Phenylquinone at a dose of 2 mg/kg was injected intraperitoneally 30 minutes after the test substance for intraperitoneal injection and 60 minutes after the test substance for oral administration, and the number of writhes exhibited during the following 5 to 10 minute period was recorded. A reduction in the number of writhes by 50% or more (≧50%) relative to the vehicle-treated group indicated possible analgesic activity.

For the tail-flick assay, groups of four male or female ICR mice weighing 22±2 g were used, and the test compound dissolved in 2% Tween 80/0.9% NaCl was administered intraperitoneally. The compound was administered intraperitoneally at 4, 8, 16 or 32 mg/kg, using 2% Tween 80—0.9% NaCl as the vehicle. Controls received vehicle alone. Morphine-HCl at a dose of 10 mg/kg was used as a positive control. At the pre-treatment point (0 minutes) a focused beam of radiant heat was applied to the middle dorsal surface of the tail to elicit a tail-flick response. This occurred within 6–7.5 seconds in pre-treated animals, and a maximum cut-off time of 15 seconds was set. The time required to elicit a pain response was recorded for each animal at 30 minutes following administration of the test compound. A prolongation of 50% or more ≧50% of the time required to elicit tail-flick response indicated possible analgesic activity.

The results for these tests are set out in Tables 2 and 3 respectively.

TABLE 2

Analgesia in the Phenylquinone Writhing Model

| Treatment | Route | Dose | N | Number of Writhings Individual | Average | % Inhibition |
|---|---|---|---|---|---|---|
| Vehicle | IP | 20 ml/kg | 1 | 19 | | |
| 2% Tween 80/ | | | 2 | 12 | | |
| 0.9% NaCl) | | | 3 | 16 | 16 | — |
| KRS-5-150 | IP | 1 mg/kg | 1 | 16 | | |
| | | | 2 | 13 | | |
| | | | 3 | 14 | 14 | 13 |
| | IP | 2 mg/kg | 1 | 13 | | |
| | | | 2 | 11 | | |
| | | | 3 | 8 | 11 | 31 |
| | IP | 4 mg/kg | 1 | 2 | | |
| | | | 2 | 11 | | |
| | | | 3 | 8 | 7 | (56) |
| | IP | 8 mg/kg | 1 | 0 | | |
| | | | 2 | 4 | | |
| | | | 3 | 2 | 2 | (88) |
| | IP | 16 mg/kg | 1 | 4 | | |
| | | | 2 | 2 | | |
| | | | 3 | 9 | 5 | (69) |
| | IP | 32 mg/kg | 1 | 0 | | |
| | | | 2 | 0 | | |
| | | | 3 | 0 | 0 | (100) |
| | IP | 64 mg/kg | 1 | Died | | |
| | | | 2 | 0 | | |
| | | | 3 | 0 | | 1/3 Died |
| | IP | 128 mg/kg | 1 | 0 | | |
| | | | 2 | Died | | |
| | | | 3 | Died | | 2/3 Died |
| Vehicle | oral | 20 ml/kg | 1 | 15 | | |
| (2% Tween 80) | | | 2 | 13 | | |
| | | | 3 | 14 | 14 | — |
| KRS-5-150 | oral | 1 mg/kg | 1 | 25 | | |
| | | | 2 | 8 | | |
| | | | 3 | 14 | 16 | 0 |
| | oral | 2 mg/kg | 1 | 9 | | |
| | | | 2 | 21 | | |
| | | | 3 | 11 | 14 | 0 |
| | oral | 4 mg/kg | 1 | 9 | | |
| | | | 2 | 15 | | |
| | | | 3 | 17 | 14 | 0 |
| | oral | 8 mg/kg | 1 | 17 | | |
| | | | 2 | 21 | | |
| | | | 3 | 6 | 15 | 0 |
| | oral | 16 mg/kg | 1 | 6 | | |
| | | | 2 | 17 | | |
| | | | 3 | 18 | 14 | 0 |
| | oral | 32 mg/kg | 1 | 12 | | |
| | | | 2 | 14 | | |
| | | | 3 | 18 | 15 | 0 |
| | oral | 64 mg/kg | 1 | 12 | | |
| | | | 2 | 5 | | |
| | | | 3 | 18 | 12 | 14 |

KRS-5-150 was active when given IP, but not when given orally. With KRS-5-150 at 128 mg/kg IP 3 of 3 test animals exhibited slight tremors, 3 of 3 test animals exhibited an increase in respiratory depth, 3 of 3 tested animals exhibited slight anoxia, and 2 of 3 animals died within 30 minutes after intraperitoneal administration.

With KRS-5-150 at 64 mg/kg IP 1 of 3 test animals died within 30 minutes after intraperitoneal administration.

TABLE 3

Analgesia in the Tail-flick Model

| Treatment | Route | Dose | N | Response Time (Seconds) 0 Time | 30 Mins. | % Inhibition |
|---|---|---|---|---|---|---|
| Vehicle | IP | 20 ml/kg | 1 | 6.4 | 6.3 | |
| (2% Tween 80/ | | | 2 | 6.2 | 6.4 | |
| 0.9% NaCl) | | | 3 | 6.4 | 6.3 | |
| | | | 4 | 6.3 | 6.4 | |
| | | | Average | 6.3 | 6.4 | 2 |
| KRS-5-150 | IP | 4 mg/kg | 1 | 6.3 | 6.2 | |
| | | | 2 | 6.4 | 6.4 | |
| | | | 3 | 6.2 | 7.4 | |
| | | | 4 | 6.3 | 6.2 | |
| | | | Average | 6.3 | 6.6 | 5 |
| | IP | 8 mg/kg | 1 | 6.3 | 6.4 | |
| | | | 2 | 6.5 | 6.8 | |
| | | | 3 | 6.3 | 6.5 | |
| | | | 4 | 6.4 | 6.7 | |
| | | | Average | 6.4 | 6.6 | 3 |
| | IP | 16 mg/kg | 1 | 6.2 | 6.3 | |
| | | | 2 | 6.3 | 6.5 | |
| | | | 3 | 6.2 | 6.2 | |
| | | | 4 | 6.4 | 6.4 | |
| | | | Average | 6.3 | 6.4 | 2 |
| | IP | 32 mg/kg | 1 | 6.5 | 6.7 | |
| | | | 2 | 6.3 | 8.7 | |
| | | | 3 | 6.3 | 6.5 | |
| | | | 4 | 6.4 | 8.4 | |
| | | | Average | 6.4 | 7.6 | 19 |
| Morphine-HCl | IP | 10 mg/kg | 1 | 6.3 | >15.0 | |
| | | | 2 | 6.2 | >15.0 | |
| | | | 3 | 6.5 | >15.0 | |
| | | | 4 | 6.3 | 9.4 | |
| | | | Average | 6.3 | 13.6 | (100) |

Significant activity in the phenylquinone-induced writing assay was observed at doses of 4, 8, 16 and 32 mg/kg following intraperitoneal administration, but not after oral administration, as shown in Table 2. Moreover, a mortality rate of ⅓ was observed at a dosage of 64 mg/kg, and a morality of ⅔ was observed at 128 mg/kg following intraperitoneal administration. In the tail-flick assay, none of the four doses used showed significant activity after intraperitoneal injection, although a slight prolongation (19%) of tail-flick response was observed at a dose of 32 mg/kg. Thus the compound is inactive compared to morphine. None of the mice given KRS-5-150 exhibited Straub tail behaviour.

The tail-flick test is thought to involve central nervous system activity, and therefore provides further confirmation of the Straub tail test.

Example 18

Analgesic Activity of KRS-6-26 and JFY-058

Testing on compounds KRS-6-26 and JFY-058 was also carried out under contract by MDS Services—Taiwan Ltd. The study was designed to evaluate the effects of the compounds as analgesics in the phenylquinone-induced writhing assay described in detail in Example 13(Siegmund et al, 1957).

In each case, a serial 2-fold dosage variance was used in the test, from 128 mg/kg to 1 mg/kg (8 doses in total). Groups of 3 male or female ICR mice weighing 22±2 g were employed. A serial 2-fold dosage variance was used in the test (8 doses in total). Variant doses (1, 2, 4, 8, 16, 32, 64 and 128 mg/kg) of test substances were administered intraperitoneally (IP). A vehicle of 2% Tween 80 in 0.9% NaCl was used for the intraperitoneal injection. The control group received vehicle alone. Phenylquinone (PQ) at dose of 2 mg/kg was injected intraperitoneally 30 minutes (IP) after test substance, and the number of writhes exhibited during the following 5–10 minute period was recorded. A reduction in the number of writhes by 50 percent or more (≧50%) relative to the vehicle-treated group indicated possible analgesic activity.

KRS-2-26

After administration by intraperitoneal injection, significant activity was found for KRS-2-26 at doses of 128, 64, 32, 16, 8, 4, 2 and 1 mg/kg. These results are summarised in Table 4. At the higher doses of 128, 64 and 32 mg/kg KRS-6-26 2 of 3 test animals exhibited slight Straub tail behaviour and piloerection. At 16 mg/kg, only one test animal exhibited slight Straub tail behaviour. There was 92% inhibition in writing in animals at 8 mg/kg and 100% at the higher doses, with no deaths. This compares very favourably against morphine, and indicates that KRS-2-26 is able to exert an analgesic effect without a central effect on the central nervous system.

JFY-058

After administration by intraperitoneal injection, significant activity was found for JFY-058 at doses of 128, 64, 32 and 16 mg/kg. These results are summarised in Table 5. None of the test animals exhibited Straub tail behaviour during the 40 minute observation period after administration, thus indicating that JFY-058 is able to exert an analgesic effect without a central effect on the central nervous system. Morphine-HCl, at 3 mg/kg produced slight Straub tail phenomenon in 2 of 3 test animals. JFY-058 compares extremely well against morphine-HCl.

TABLE 4

Analgesia in the Phenylquinone Writhing Model-KRS-6-26

| Treatment | Route | Dose | N | Number of Writhings Individual | Average | % Inhibition |
|---|---|---|---|---|---|---|
| Vehicle | IP | 10 ml/kg | 1 | 10 | | |
| 2% Tween 80/ | | | 2 | 15 | | |
| 0.9% NaCl) | | | 3 | 12 | 12 | — |
| KRS-6-26 | IP | 1 mg/kg | 1 | 0 | | |
| | | | 2 | 13 | | |
| | | | 3 | 4 | 6 | 50 |
| | IP | 2 mg/kg | 1 | 13 | | |
| | | | 2 | 2 | | |
| | | | 3 | 4 | 6 | 50 |
| | IP | 4 mg/kg | 1 | 0 | | |
| | | | 2 | 7 | | |
| | | | 3 | 2 | 3 | 75 |
| | IP | 8 mg/kg | 1 | 1 | | |
| | | | 2 | 0 | | |
| | | | 3 | 2 | 1 | 92 |
| | IP | 16 mg/kg | 1 | 0 | | |
| | | | 2 | 0 | | |
| | | | 3 | 0 | 0 | 100 |
| | IP | 32 mg/kg | 1 | 0 | | |
| | | | 2 | 0 | | |
| | | | 3 | 1 | 0 | 100 |
| | IP | 64 mg/kg | 1 | 0 | | |

TABLE 4-continued

Analgesia in the Phenylquinone Writhing Model-KRS-6-26

| Treatment | Route | Dose | N | Number of Writhings Individual | Average | % Inhibition |
|---|---|---|---|---|---|---|
| | | | 2 | 0 | | |
| | | | 3 | 0 | 0 | 100 |
| | IP | 128 mg/kg | 1 | 0 | | |
| | | | 2 | 0 | | |
| | | | 3 | 0 | 0 | 100 |
| Morphine | IP | 3 mg/kg | 1 | 1 | | |
| | | | 2 | 0 | | |
| | | | 3 | 0 | 0 | 100 |

TABLE 5

Analgesia in the Phenylquinone Writhing Model-JFY-058

| Treatment | Route | Dose | N | Number of Writhings Individual | Average | % Inhibition |
|---|---|---|---|---|---|---|
| Vehicle | IP | 10 ml/kg | 1 | 17 | | |
| 2% Tween 80/ | | | 2 | 29 | | |
| 0.9% NaCl) | | | 3 | 22 | 23 | — |
| JFY-058 | IP | 1 mg/kg | 1 | 17 | | |
| | | | 2 | 19 | | |
| | | | 3 | 10 | 15 | 17 |
| | IP | 2 mg/kg | 1 | 15 | | |
| | | | 2 | 13 | | |
| | | | 3 | 8 | 12 | 33 |
| | IP | 4 mg/kg | 1 | 15 | | |
| | | | 2 | 6 | | |
| | | | 3 | 11 | 11 | 39 |
| | IP | 8 mg/kg | 1 | 3 | | |
| | | | 2 | 15 | | |
| | | | 3 | 14 | 11 | 39 |
| | IP | 16 mg/kg | 1 | 2 | | |
| | | | 2 | 1 | | |
| | | | 3 | 8 | 4 | 78 |
| | IP | 32 mg/kg | 1 | 0 | | |
| | | | 2 | 0 | | |
| | | | 3 | 1 | 0 | 100 |
| | IP | 64 mg/kg | 1 | 0 | | |
| | | | 2 | 0 | | |
| | | | 3 | 0 | 0 | 100 |
| | IP | 128 mg/kg | 1 | 0 | | |
| | | | 2 | 0 | | |
| | | | 3 | 0 | 0 | 100 |
| Morphine | IP | 3 mg/kg | 1 | 0 | | |
| | | | 2 | 0 | | |
| | | | 3 | 0 | 0 | 100 |

Example 19

In Vitro Opiate Receptor Binding Assays

To characterise the target specificity of the compounds, KRS-5-150 and KRS-6-26 were tested at a concentration of 10 μM for their ability to inhibit the binding of a radioligand to human δ-, κ-, or μ-opiate receptors in vitro using commercially available assays (MDS Pharma Services; assay catalogue numbers 260110, 260210 and 260410 respectively).

The results of these assays are presented below. Percentage inhibition of radioligand binding to human opioid receptors in vitro by test compounds (10 μM)

| | Test compound KRS-5-150 | KRS-6-26 |
|---|---|---|
| δ-opiate receptor | 79 | 95 |
| κ-opiate receptor | 79 | 94 |
| μ-opiate receptor | 98 | 99 |

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein and below and are incorporated herein by this reference. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in Australia or in any other country.

REFERENCES

Barvian, M. R et al Tetrahedron Letters, 38 6799–6802, 1997.

D'Amour, F. E. and Smith, D. L. A method for determining loss of pain sensation. *J. Pharmacol. Exp. Ther.* 72: 74–79, 1941.

Maryanoff, C. A. et al J. Org. Chem., 51, 1882–1884, 1986.

Palomo C. and Mestres R., *Synthesis* 373, 1981.

Reddy L. N. et al J. Med. Chem. 37, 260–267, 1994

Ramadas K. et al, Tetrahedron Letters 42, 343–346, 2001.

Siegmund, E., Cadmus, R. and Lu, G. A method for evaluating both non-narcotic and narcotic analgesics. Proc. Soc. Exp. Biol. Med. 95, 729–731, 1957.

The claims defining the invention are as follows:

1. A compound of formula I

I

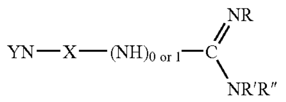

in which

YN is a morphine-like opioid radical of Formula II

II

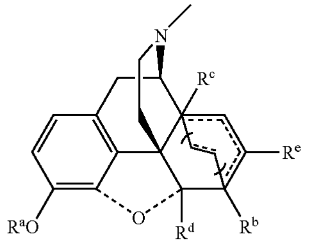

wherein:

$R^a$ is H, $C_{1-4}$alkyl, $C_{1-4}$alkanoyl, $C_{1-4}$carboxyalkyl, or an O— protecting group;

$R^b$ is H, OH, protected hydroxy, $C_{1-4}$alkanoyloxy or $C_{1-4}$alkoxy; or, when C6 does not have a double bond to C7, and does not have an endoetheno or endoethano bridge to C14, $R^b$ may be =O or $=CH_2$;

$R^c$ is absent, or, when C6 does not have a double bond to C7, and does not have an endoetheno or endoethano bridge to C14, $R^c$ is H, OH or protected hydroxy;

$R^d$ is H or $C_{1-4}$ alkyl;

$R^c$ is H, CN, $C_{1-4}$alkanoyl, $C_{1-4}$alkoxycarbonyl, $C_{2-8}$ alkenyl,

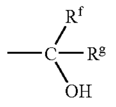

in which $R^f$ is H, alkyl, aryl, or alkaryl, and $R^g$ is $C_{1-8}$ alkyl, $C_{2-6}$alkenyl, $C_{2-6}$alkenyl, each of these three groups being optionally substituted by aryl, or $R^g$ is substituted aryl (the substituent(s) on the aryl group being chosen from halo, alkyl, $C_{1-4}$alkoxy, haloalkyl), tetrahydrofuranyl, $C_{1-4}$ alkoxy; and wherein the oxygen between C4 and C5 may or may not be present, as represented by the broken lines; wherein the brackets around the group between C6 and C14 represents that the group may or may not be present, and when present the group may be an endoetheno or an endoethano bridge, as represented by the broken line; and wherein the dashed line between C6, C7, C8 and C14 represents that there is or are either zero, one or two double bonds, with the one double bond being either between C6 and C7, or C7 and C8, and the two double bonds being between C6 and C7, and C8 and C14;

X is—a direct bond, an optionally substituted, branched, straight-chained or cyclic alkylene having from 1 to 6 carbon atoms, optionally containing one or two heteroatoms in the alkyl chain, or an optionally substituted, branched or straight-chained alkenylene having from 4 to 10 carbon atoms; and R, R' and K" are independently hydrogen, alkyl, substituted alkyl, alkene, substituted alkene, alkyne, substituted alkyne, aryl, substituted aryl, heterocycle, substituted heterocycle or cyano provided that at least one of R and R' is aryl, substituted aryl, heterocycle or substituted heterocycle which is directly attached to the nitrogen atom of the guanidine group through an atom of the aryl or heterocycle group;

or a pharmaceutically acceptable salt, hydrate, solvate, tautomer and/or isomer thereof.

2. A compound according to claim 1, in which R is H, alkyl, phenyl, substituted phenyl, heterocycle or substituted heterocycle.

3. A compound according to claim 1, in which R' is phenyl, substituted phenyl, heterocycle or substituted heterocycle.

4. A compound according to claim 1, in which R" is H, alkyl, phenyl, substituted phenyl, heterocycle or substituted heterocycle.

5. A compound according to claim 1, in which at least one of R' and R" is not H.

6. A compound according to claim 1, in which the heterocycle or substituted heterocycle is heteroaromatic or substituted heteroaromatic, respectively.

7. A compound according to claim 1, in which at least one of X, R, R', and R are substituted with at least one substituent selected from the group consisting of halo, alkyl, alkene, alkyne, aryl, heterocyclic, haloalkyl, haloalkene, haloalkyne, acyl, acyloxy, hydroxy, amino, substituted amino groups, nitro, thio, alkylthio, carboxy, sulphonic acid, sulphoxides, sulphonamides, quaternary ammonium groups, alkoxy groups, and combinations thereof.

8. A compound according to claim 1, in which the substituent on the aryl or heteroaryl group is a $C_{1-6}$ alkyl group, haloalkyl, hydroxy, amino, alkoxy, haloalkoxy, nitro, alkylthio, thiol or halo.

9. A compound according to claim 1, in which the radical YN— is a radical selected from the group consisting of

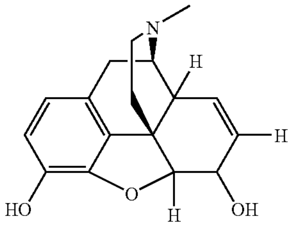

morphine,

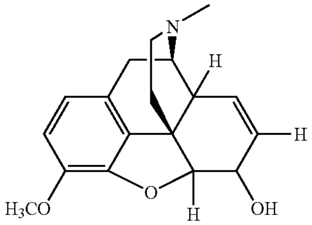

codine,

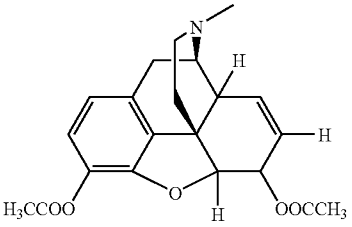

heroin,

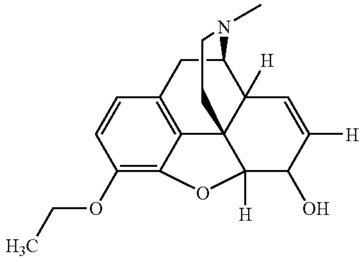

ethylmorphine,

-continued
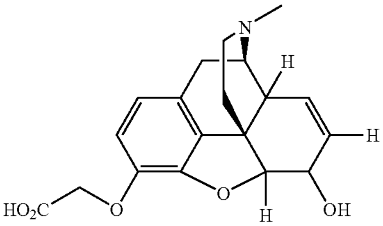
O-carboxymethylmorphine,
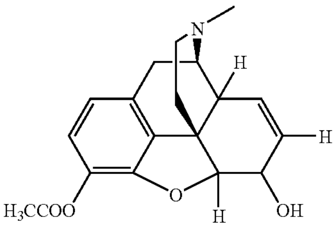
O-acetlmorphine,
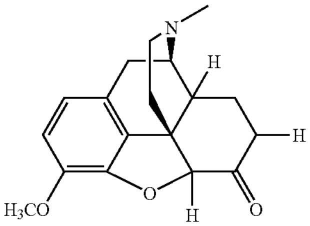
hydrocodone,
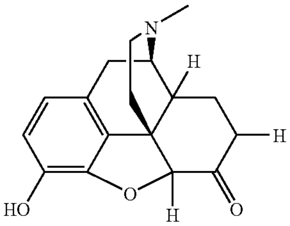
hydromorphone,
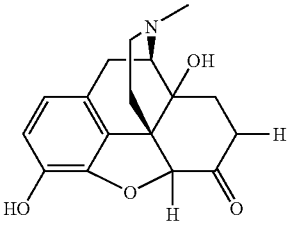
oxymorphone,
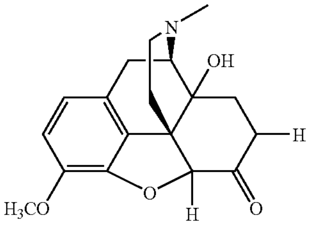
oxycodone,
-continued
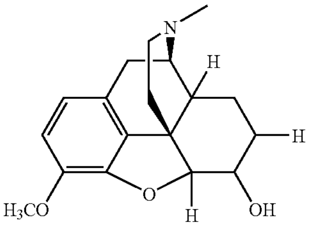
dihydrocodeine,
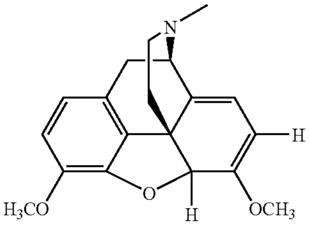
thebaine,
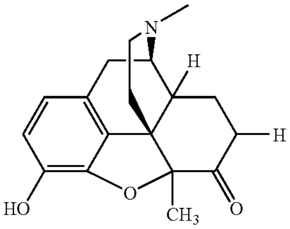
metopon,
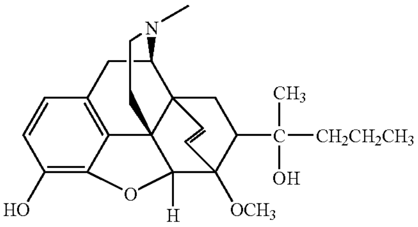
etorphine,
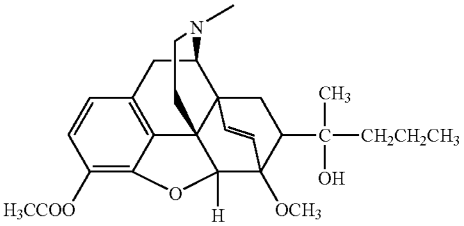
acetorphine,
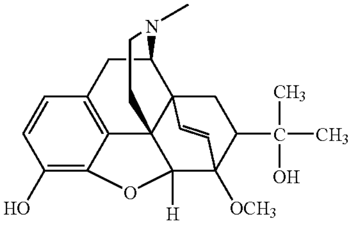
diprenorphine, -continued
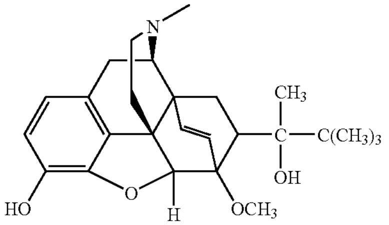
buprenorphine,
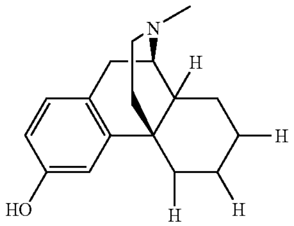
phenomorphan,
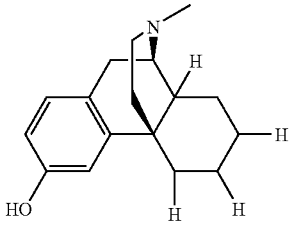
levorphanol,
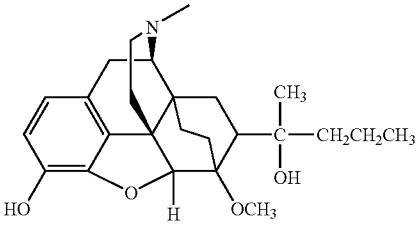
dihydroetorphine, and
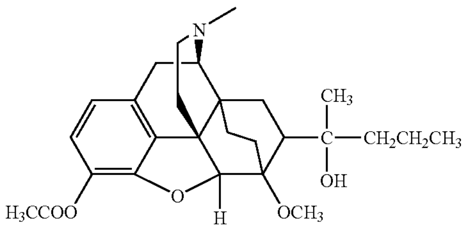
dihydroacetorphine.
10. A compound according to claim 1, in which the radical YN— is a radical of
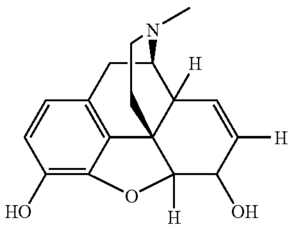
morphine,
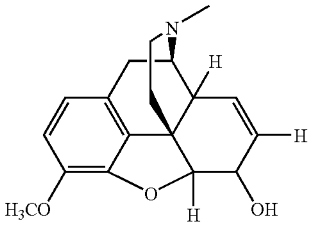
codeine,
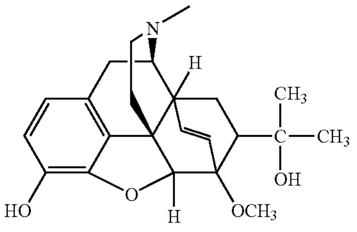
diprenorphine, or
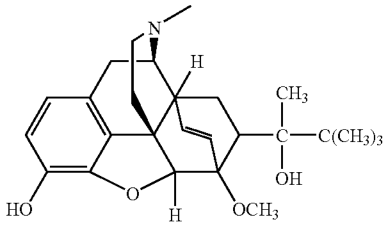
buprenorphine.
11. A compound according to claim 1, selected from the group consisting of the following formulae:
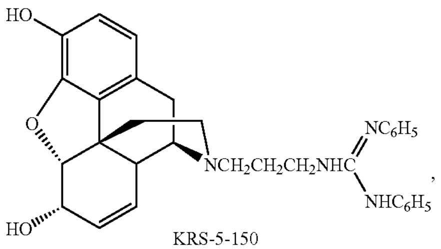
KRS-5-150

-continued

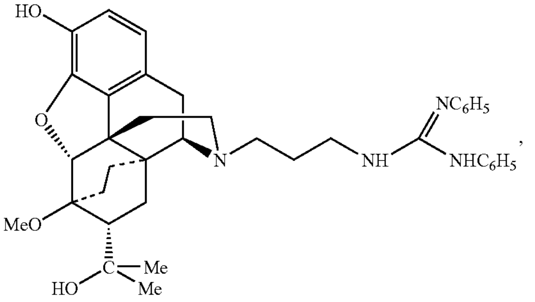

KRS-6-79

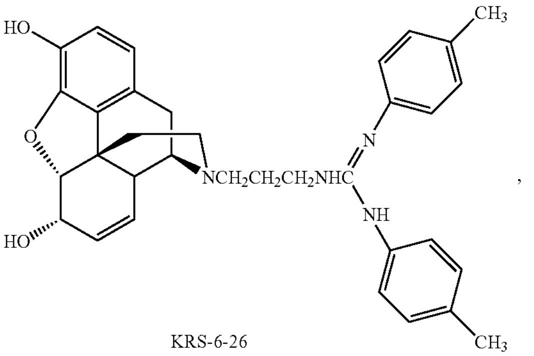

,

KRS-6-26

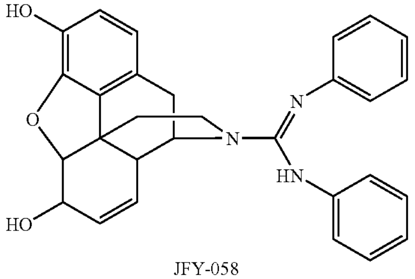

, and

JFY-058

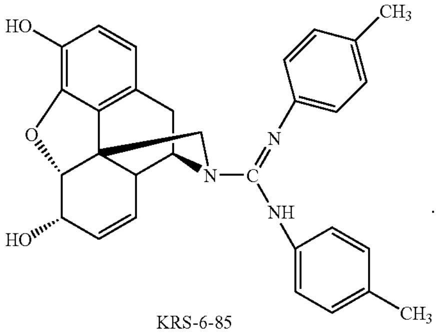

.

KRS-6-85

12. A process for the preparation of a compound of formula I as defined in claim 1 comprising:

(a) reacting a precursor for the radical YN—X—$(NH)_{0\ or\ 1}$ with a precursor for the radical

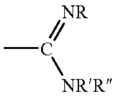

which comprises one of the following:

(i) reacting YN—H or YN—X—$NH_2$ with a compound of formula

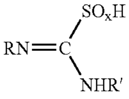

in which x is 2 or 3, to form a compound of formula I in which R" is H;

(ii) reacting YN—H or YN—X—$NH_2$ with cyanogen bromide to give a cyanamide (YN—CN or YN—X—NH—CN) and then reacting the cyanamide with R'$NH_2$Z in which Z is an acid addition salt, to form a compound of formula I in which R is H and R" is H;

(iii) reacting YN—H or YN—X—$NH_2$ with RN═C═NR' to form a compound of formula I in which R" is H;

(iv) reacting YN—H or YN—X—$NH_2$ with a compound of formula 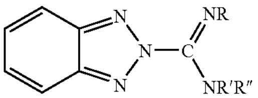 and/or formula 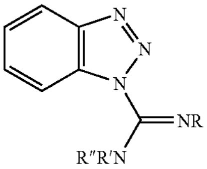

(b) reacting a precursor for the radical YN— with a precursor for the radical

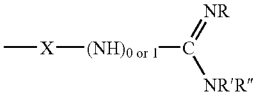

I in which YN—, X, R, R' and R" areas defined in formula I, which comprises:

(1) reacting the compound [hydroxy protecting group]-O—X—$NH_2$ with (i) a compound of formula

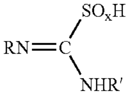

in which x is 2 or 3;

(ii) RN═C═NR'; or (iii) a compound of formula 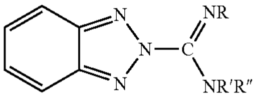 and/or

-continued formula 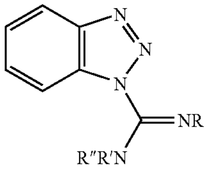

to form a compound of formula IV

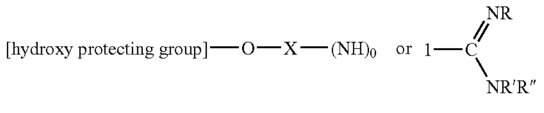

(2) removing the hydroxy-protecting group from the compound of formula IV and brominating the deprotected compound, thereby forming a brominated product; and (3) reacting the brominated product with YN—H to form the compound of formula I.

13. A composition comprising a compound of formula I as defined in claim 1, together with a pharmaceutically or veterinarily acceptable carrier.

14. A method of inducing analgesia comprising administering a therapeutically effective amount of a compound of formula I as defined in claim 1 to a subject in need thereof.

15. A method according to claim 14, comprising inducing analgesia in the peripheral nervous system.

16. A method according to claim 14, in which the compound of formula I is administered orally or parenterally.

* * * * *